United States Patent [19]

Vilas

[11] Patent Number: 5,411,504
[45] Date of Patent: May 2, 1995

[54] DRILL JIG FOR ANIMAL PROSTHESIS INSERTION

[76] Inventor: John W. Vilas, 2007 Vinewood Dr., Bryan, Tex. 77802

[21] Appl. No.: 101,445
[22] Filed: Aug. 2, 1993
[51] Int. Cl.⁶ ............................ A61F 5/00; A61F 2/32
[52] U.S. Cl. ........................................ 606/87; 606/96
[58] Field of Search ................ 606/96, 97, 98, 86, 606/87, 88, 80, 79

[56] References Cited
U.S. PATENT DOCUMENTS

| | | | |
|---|---|---|---|
| 3,782,373 | 1/1974 | Smythe | 606/98 |
| 4,644,943 | 2/1987 | Thompson | 606/98 |
| 4,881,535 | 11/1989 | Sohngen | 606/98 |
| 4,913,137 | 4/1990 | Azer | 606/96 |
| 4,985,032 | 1/1991 | Goble | 606/96 |
| 5,152,764 | 10/1992 | Goble | 606/98 |
| 5,207,682 | 5/1993 | Cripe | 606/96 |
| 5,234,434 | 8/1993 | Goble | 606/98 |

Primary Examiner—Michael A. Brown
Attorney, Agent, or Firm—David H. Judson

[57] ABSTRACT

A drill jig suitable for use during the insertion of a prosthesis or implant in an animal and a method of using the drill jig are provided. The drill jig includes a first member, a second member and a shank connecting the members. The distance between the first and second members may be adjusted to facilitate insertion requirements or to accommodate individual animal characteristics.

14 Claims, 3 Drawing Sheets

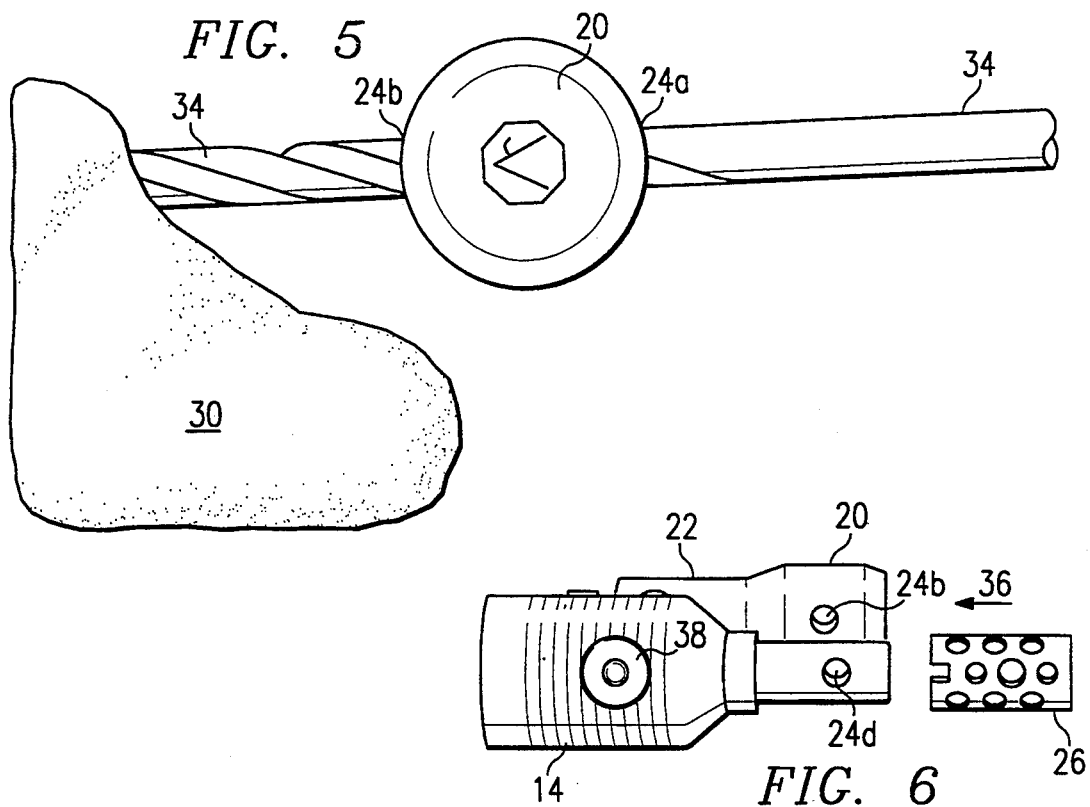
FIG. 5
FIG. 6
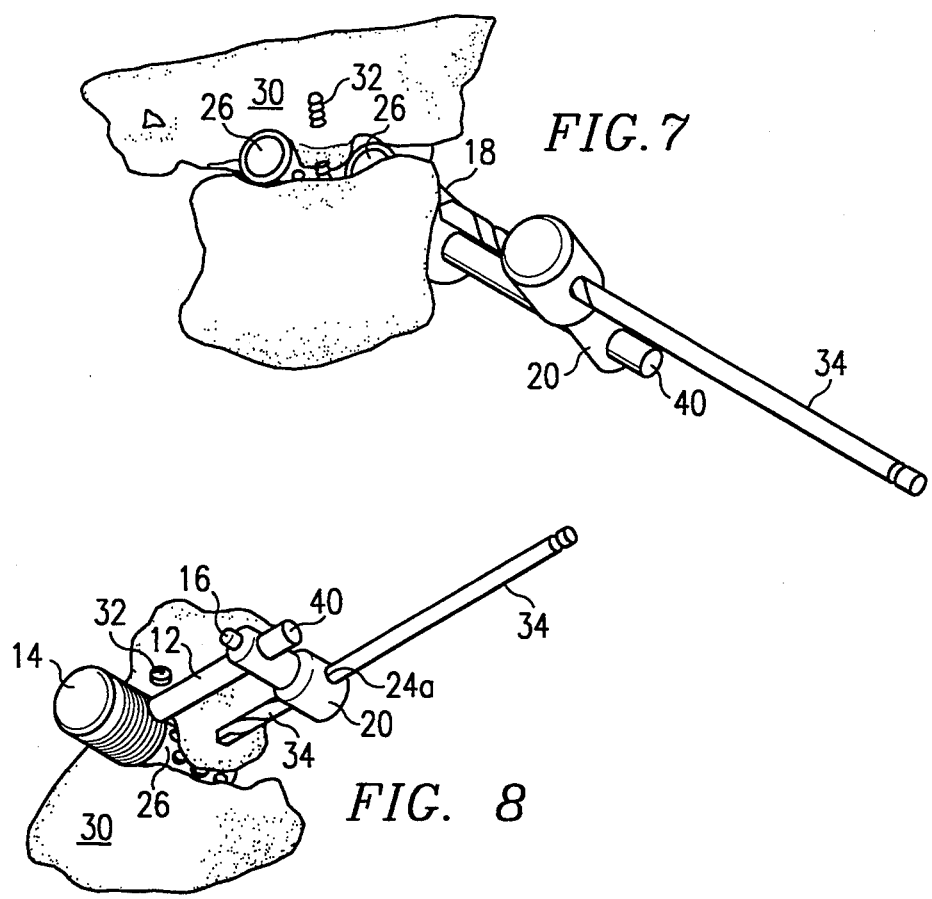
FIG. 7
FIG. 8

DRILL JIG FOR ANIMAL PROSTHESIS INSERTION

TECHNICAL FIELD

The present invention relates generally to drill jigs and more specifically to drill jigs for use in placing intra-articular prostheses or implants into the distal interphalangeal joint of an equine or other similarly hoofed animal.

BACKGROUND OF THE INVENTION

Drill jigs are well-known in the prior art. For example, U.S. Pat. No. 3,782,373 to Smythe discloses a drill jig for a femoral prosthesis. The jig includes a plurality of drill guide bores formed therein which coincide or match with a plurality of bores in the prosthesis. The jig is then used to drill bores in the bone to the existing holes in the prosthesis.

It is also known in the prior art to use drill jigs for total hip prosthesis. U.S. Pat. No. 3,814,089 to Deyerle relates to a U-shaped drill jig having a long leg with drill holes. These holes can be aligned with the holes in the prosthesis shank to permit screws to be placed in the prosthesis holes. Additionally, U.S. Pat. No. 4,913,137 to Azer et al. teaches the use of an intramedullary rod system to align a drill with holes in a bone implant or insert for the fixation of long, hollow bones, such as a femur.

It is further known in the art to use tubular sleeves for bone grafting in animals. The sleeves include holes or perforations to allow bone grafts to move outward and fuse the joint. However, restorative surgeries of this nature have typically required immobilizing the animal in a cast for up to six weeks. Consequently, prior art techniques of fusing the coffin bone joint in a horse or other similarly hoofed animal have proved insufficient since immobilizing the animal for relatively long periods of time is impractical and inconvenient.

Another disadvantage associated with the prior art has been the inability or lack of precision in locating the position of holes to be drilled through a bone such that the holes would thereafter be accurately aligned with preformed holes or openings in a prosthesis. This is in part due to the lack of a releasably assembled drill jig suitable for placing an implant into the coffin bone joint of a horse or other similarly hoofed animal which overcomes the problems associated with the prior art. It would therefore be desirable to provide a drill jig which is suitable for use with horses and other such animals that is capable of being releasably attached to a prosthesis during insertion such that fusion could be achieved with a minimum loss of mobility to the animal.

BRIEF SUMMARY OF THE INVENTION

It is thus an object of the present invention to provide a drill jig for placing a prosthesis in a horse or other animal.

It is another object of the present invention to provide a drill jig capable of placing an intra-articular implant into the distal interphalangeal joint of an equine.

It is another object of the present invention to provide a drill jig that may be used with a mallet or the like.

It is another object of the present invention to provide a drill jig that is releasably attached to a prosthetic device to provide a guide for locating drilled holes in the prosthesis.

It is yet another object of the present invention to provide a drill jig which is capable of indexing the prosthesis to align a drill bit with a single oversized hole in the prosthesis.

It is a further object of the present invention to provide a drill jig which permits a hole to be drilled in a horse abaxial to axial from the head of the middle phalange to the base of the distal phalange in an oblique line.

It is yet a further object of the present invention to provide a drill jig which can be adjusted to account for individual bone characteristics of the animal during insertion.

It is still a further object of the present invention to provide a method of using a drill jig to insert a prosthesis in an equine or similar animal which requires less immobilization and less restraint of the animal during the fusion and recovery processes than that required using prior art techniques.

These and other objects of the invention are provided in a drill jig which includes a shank, a first member and a second member. The jig indexes a prosthesis having a perforated tubular sleeve to align a drill bit with a single oversized hole in the implant, thereby enabling insertion of the sleeve in an animal using a mallet or the like and further enabling a hole to be drilled abaxial to axial from the head of the middle phalange through the bone to the base of the distal phalange in an oblique line. A locking mechanism, such as a lag screw, is then installed through the implant securing the joint and preventing the implant from migrating.

Once the perforated sleeve and locking mechanism are in place, the sleeve is packed with bone marrow, thereby causing growth and fusion of the sleeve with the joint such that the sleeve does not migrate. After a few days, the animal no longer need be confined. The sleeve is thus permanently fused to the joint while the drill jig is removed immediately following insertion.

The drill jig is preferably formed of stainless steel, thereby capable of withstanding the impact of a mallet or the like. In a preferred embodiment, the distance between the first and second members is adjustable to account for size differences or other individual requirements of the animal. In accordance with yet a further feature of the invention, the drill jig can be adjusted to account for size differences in individual animals and/or requirements for insertion.

The foregoing has outlined some of the more pertinent objects of the present invention. These objects should be construed to be merely illustrative of some of the more prominent features and applications of the invention. Many other beneficial results can be attained by applying the disclosed invention in a different manner or modifying the invention as will be described. Accordingly, other objects and a fuller understanding of the invention may be had by referring to the following Detailed Description of the preferred embodiment.

BRIEF DESCRIPTION OF THE DRAWINGS

For a more complete understanding of the present invention and the advantages thereof, reference should be made to the following Detailed Description taken in connection with the accompanying drawings in which:

FIG. 5 illustrates a bottom view of the second housing of a drill jig in accordance with the present invention and a drill bit being inserted through the second housing and into the coffin bone joint of an equine;

FIG. 6 is a side view of a drill jig and a tubular prosthesis according to the present invention as viewed from the side nearest the first member of the drill jig;

FIG. 7 is a bottom perspective view of a drill jig as it is used to insert a tubular sleeve prosthesis in accordance with the present invention;

FIG. 8 is a top perspective view of FIG. 7; and

Similar reference characters refer to similar parts throughout the several views of the drawings.

DETAILED DESCRIPTION

In accordance with the present invention, a drill jig is provided that is useful in inserting an intra-articular implant into a joint of a hoofed animal. While the invention is not so limited, the drill jig is preferably used to insert an implant into the distal interphalangeal joint of an equine. The present invention further includes a method of inserting such an implant which is relatively simple to use.

Figure 1:
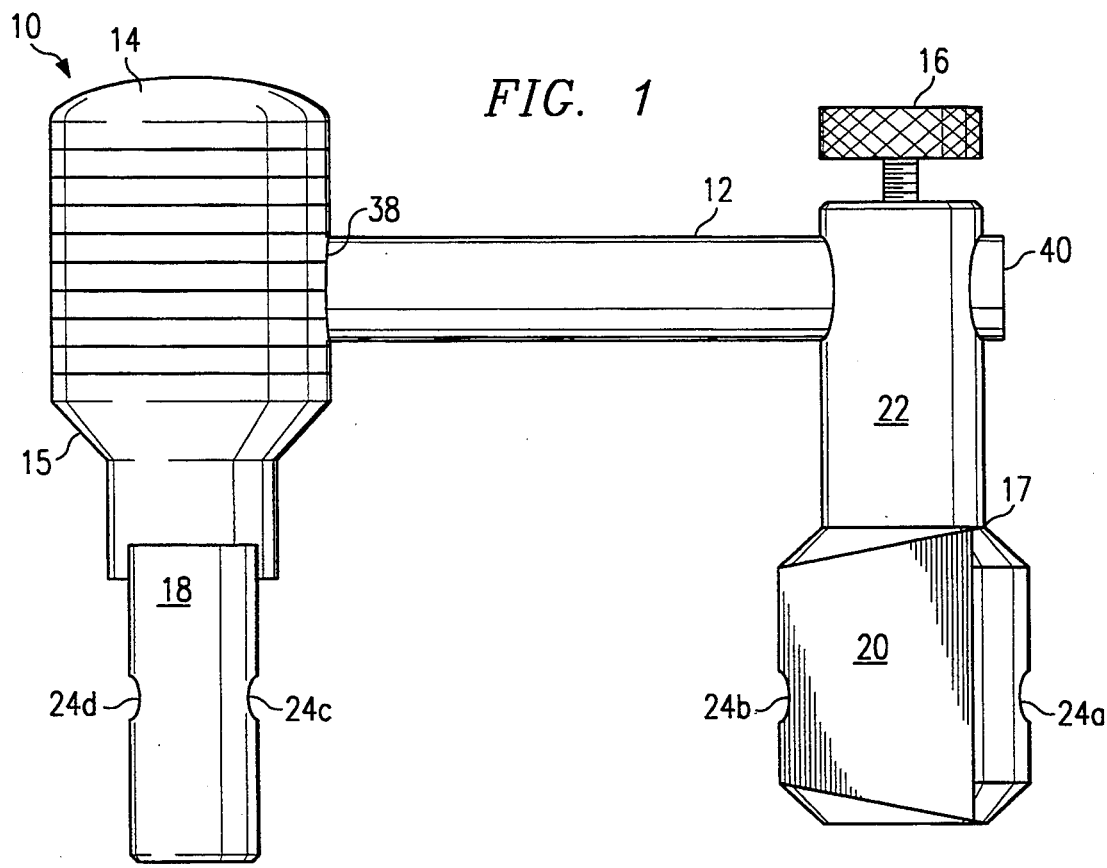
FIG. 1 is a front view of a drill jig in accordance with the present invention.
Figure 2:
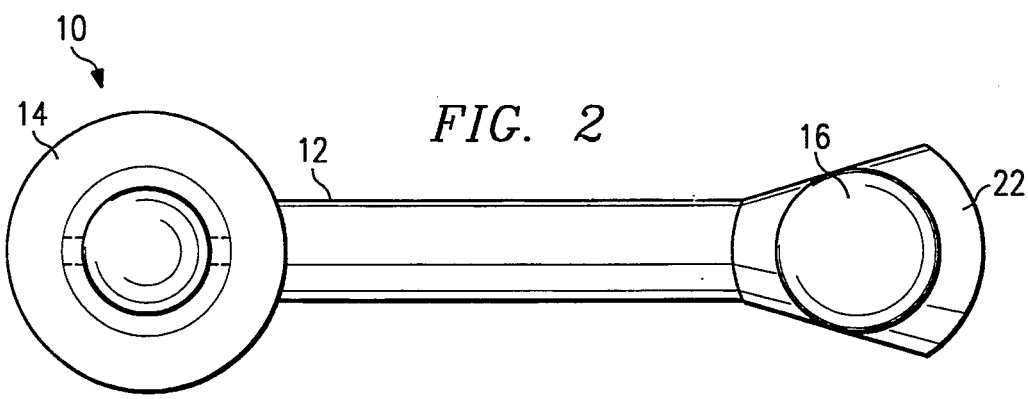
FIG. 2 is a top view of the drill jig illustrated in FIG. 1.

Reference is now had to FIGS. 1 and 2 in which front and top views of a drill jig 10 in accordance with the present invention are illustrated. Jig 10 includes a first member 15, an elongated shank 12 and a second member 17. A first tube or leg 18 extends vertically downward from first housing 14 while a second tube or leg 22 extends vertically upward from second housing 20.

Shank 12 includes a first end 38 attached to first housing 14 and a second end 40 attached to second leg 22 such that shank 12 extends approximately perpendicular to first and second housings 14, 20 and first and second legs 18, 22. Ends 38, 40 of shank 12 may be directly attached to first housing 14 and second leg 22 respectively, such that end 38 abuts the outer surface of first housing 14 while end 40 abuts the outer surface of second leg 22. As shown in FIGS. 1 and 2, however, second leg 22 preferably includes a locking member 16 attached to the end opposite second housing 20 and an opening or bore such that shank 12 is slidably adjustable within leg 22. This provides the advantage of allowing for variations in individual animals and insertion procedures. Once the appropriate distance between first housing 14 and second housing 20 is determined, locking member 16 is activated to secure shank 12 in place. Locking member 16 may be a screw or the like. In another preferred embodiment, first housing 14 includes an opening or bore such that shank 12 is slidably adjustable along the horizontal axis in either direction. As shown in FIG. 6, first end 38 of shank 12 is thus capable of extending through first housing 14 to increase or decrease the distance between first and second housings 14 and 20. This is particularly advantageous where the insertion procedure requires adjustment of the jig around a structure or sensitive area and adjustment of the second housing 20 or leg 22 is impractical.

Referring to FIG. 1, openings 24a-24d are shown. Openings 24a-24d extend along the horizontal axis such that a drill bit may be positioned and extended therethrough. Preferably, the diameter of openings 24a-24d is in the range of 4.5 to 6 mm. Openings 24a-24d provide for jig 10 to index an implant to align the drill bit with a single oversized hole in the implant, thereby enabling a hole to be drilled abaxial to axial from the head of the middle phalange to the base of the distal phalange in an oblique line. The drill bit and jig are removed and a locking mechanism such as a lag screw may then be installed through the implant to secure the joint and prevent the implant from migrating.

Figure 3A:
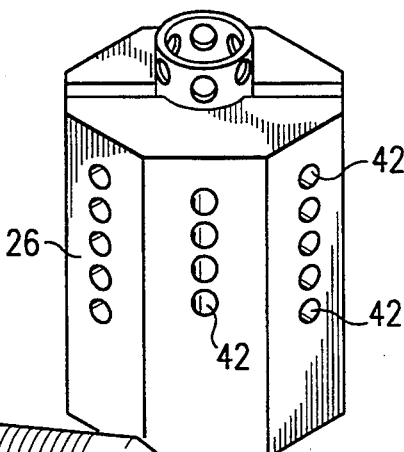
FIG. 3A is a perspective side view of a drill jig and a perforated tubular sleeve prosthesis according to the teachings of the present invention.
Figure 3A:
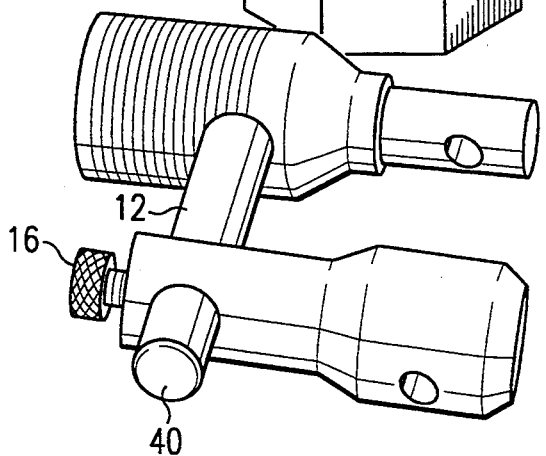
Figure 3B:
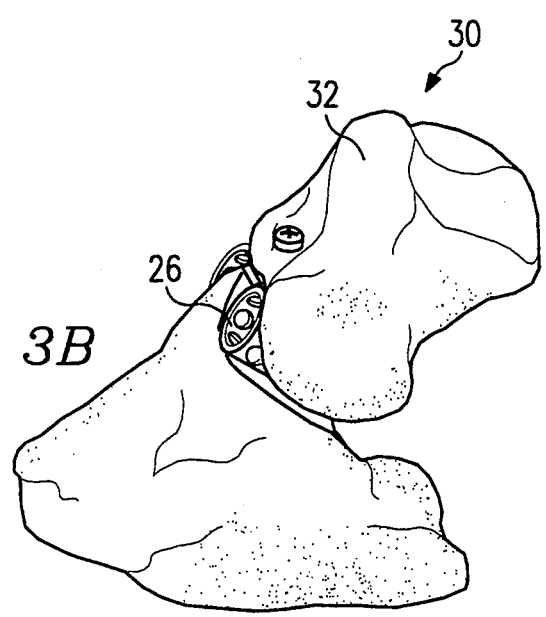
FIG. 3B illustrates a perforated sleeve prosthesis and lag screw inserted into the coffin bone joint of an equine.

FIG. 3A is a side view of jig 10 showing end 40 of shank 12 extending through second leg 22. FIG. 3A also illustrates a perforated tubular sleeve prosthesis 26 which is suitable for use in the present invention. Prosthesis 26 includes a plurality of holes 42. Prosthesis 26 is placed over first leg 18 and positioned such that one of the holes 42 is aligned with hole 24c. Holes 42 allow for the lag screw to be inserted through prosthesis 26. Additionally, holes 42 provide for growth and fusion of bone marrow transport after insertion of prosthesis 26. As shown in FIG. 3B, prosthesis 26 and lag screw 32 may be inserted into the coffin bone joint 30 of an equine and left in position permanently without discomfort or loss of mobility to the horse.

Figure 4:
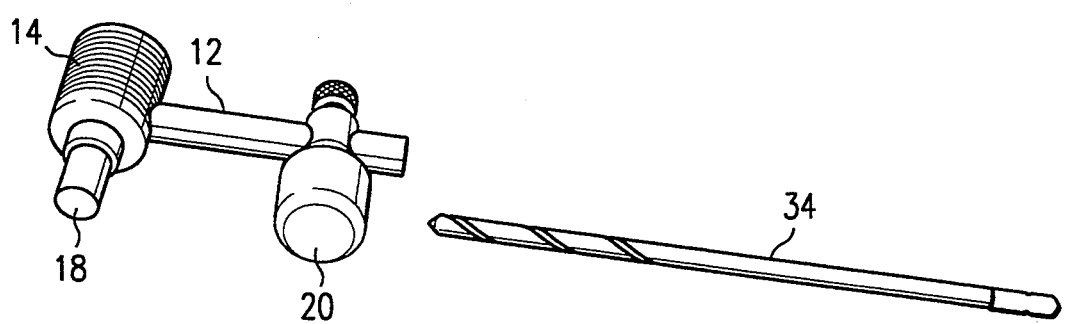
FIG. 4 is a perspective bottom view of a drill jig and a side view of a drill bit according to the present invention.

Referring now to FIG. 4 in which a bottom view of jig 10 is illustrated. As can be seen, the bottom of second housing 20 is a smooth surface. This is beneficial in that a mallet or the like may be used to force second housing 20 in a position to align holes 24a-24d with a hole 42. Once the prosthesis is positioned as discussed above, drill bit 34 may be inserted through holes 24a-24d to properly drill a hole for a lag screw aligned with one of the holes 42.

A bottom view of jig 10 is shown in FIG. 5 as it is used in accordance with the invention. Drill bit 34 extends through holes 24a-24b of first housing 20. Bit 34 is then drilled into a predetermined position in bone 30 such that the hole drilled in bone 30 will be properly aligned with a hole 42 in prosthesis 26 (not shown in FIG. 5).

A side view of an alternative embodiment as viewed from the side closest to the first housing 14 of jig 10 is illustrated in FIG. 6. In this embodiment, first end 38 of shank 12 is positioned to extend through two openings in first housing 14. This enables shank 12 to be slidably adjusted horizontally either towards first housing 14 or second housing 20. Locking member 16 is then used to secure shank 12 in place during the insertion process. Consequently, hard to reach places and/or individual needs of the animal can be more readily provided for. After positioning shank 12, prosthesis 26 is placed over leg 18 by moving it in a direction 36 and a hole 42 is aligned with holes 24c and 24d. The jig and prosthesis are then ready for insertion into the animal.

Reference is now had to FIG. 7 in which a bottom view of a drill jig in accordance with the present invention is shown as it used for inserting a prosthesis 26 into an equine. As shown in FIG. 7, it is sometimes necessary to insert two or more tubular sleeve prostheses 26. Lag screw 32 is illustrated in FIG. 7 in bone 30. First leg 18 of jig 10 is shown with a second prosthesis 26 being inserted into the coffin bone joint of a horse. As mentioned above, the position of second housing 20 may be adjusted using a mallet or the like such that drill jig 34 is properly aligned with a hole 42 in prosthesis 26. Additionally, second end 40 of shank 12 may be adjusted during insertion if necessary using locking member 16.

FIG. 8 is a top view of the insertion shown in FIG. 7. Drill bit 34 is shown extending through bone 30 into prosthesis 26. After lag screw 32 is properly inserted, jig 10 is released from prosthesis 26 and removed. The top of first housing 14 may be adjusted using a mallet or the like in a similar manner as discussed in reference to second housing 20.

Figure 9:
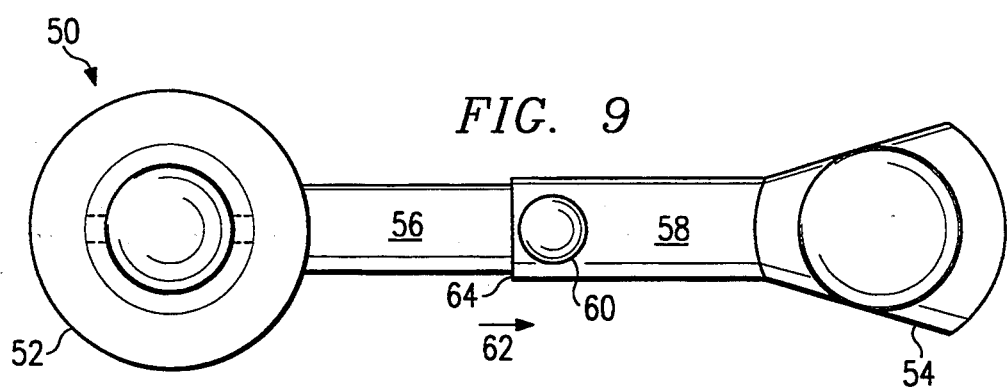
FIG. 9 is a top view of an alternative embodiment of the present invention.

Yet another alternative embodiment of the present invention is shown in FIG. 9 which is a top view of drill jig 50. In this embodiment, jig 50 includes first member 52, second member 54, shank 64 and locking member 60. However, shank 64 includes first piece 56 and second piece 58 having a larger diameter than first piece 56. Variations in distance between first and second members 52 and 54 are accomplished by releasing or loosening locking member 60, adjusting first piece 56 accordingly and then engaging locking member 60. In this embodiment, locking member 60 is preferably attached to second piece 58. For example, if the distance between first and second members is to be reduced, first piece 56 is moved in a direction 62. Conversely, if the distance between members 52 and 54 is to be enlarged, first piece 56 is moved in a direction opposite 62.

The drill jig in accordance with the present invention functions as follows. The coffin bone joint is prepared for insertion using preoperative restorative surgery procedures. The distance between the first and second members of the drill jig is adjusted to a predetermined distance. A perforated tubular sleeve prosthesis is then inserted over the first leg and positioned such that a hole in the prosthesis is aligned with the holes in the first leg of the jig. A drill bit is then inserted through the second housing of the jig and through the holes in the first leg and the prosthesis in the aligned position. Any refinements to insure that the drill bit is properly aligned is then done.

While the drill jig, prosthesis and drill bit are in the aligned position, a hole is drilled abaxial to axial from the head of the middle phalange to the base of the distal phalange in oblique line. The drill jig and drill bit are then removed and a lag screw or the like is installed through the prosthesis opening, thereby securing the joint and preventing the prosthesis from migrating.

It should be appreciated by those skilled in the art that the specific embodiments disclosed above may be readily utilized as a basis for modifying or designing other structures for carrying out the same purposes of the present invention. For example, the drill jig may be modified for use in connection with prostheses for insertion in other joints or in other animals. It should also be realized by those skilled in the art that such equivalent constructions do not depart from the spirit and scope of the invention as set forth in the appended claims.

What is claimed is:

1. A jig for inserting an implant into an animal, the jig comprising:
   a first member comprising a first housing and a first leg having a first end and a second end, the second end extending vertically downward from the housing, the first leg having a plurality of openings extending therethrough along an axis perpendicular to the first leg and adapted to receive a prothesis having openings formed therethrough such that one of the openings in the prostesis is aligned with one of the opening in the first leg;
   an elongated shank having first and second ends, the first end attached to the first housing; and
   a second member comprising a second housing and a second leg having a first end and a second end, the second leg attached to the second end of the shank, the second end of the second leg extending vertically upward from the second housing and the housing having a plurality of openings extending therethrough in a direction perpendicular to the second leg and along the same axis as the openings in the first leg.

2. The jig as described in claim 1 wherein the openings of the legs are adapted to receive a drill bit.

3. The jig as described in claim 2 wherein the openings have a diameter of approximately 4.5 mm.

4. The jig as described in claim 1 wherein the jig is formed of stainless steel.

5. The jig as described in claim 1 further including slidable means, such that the first and second ends of the shank may be positioned to vary the distance between the first and second members.

6. The jig as described in claim 5 wherein the slidable means includes a locking member attached to the second end of the second leg, openings extending through the first housing and adapted to receive the first end of the shank therethrough and openings extending through the second leg and adapted to receive the second end of the shank therethrough.

7. The jig as described in claim 5 wherein the slidable means is a locking member and wherein the shank comprises first and second pieces, the first piece having a smaller diameter than the second piece such that the first piece is slidably positioned within the second piece and secured therein by the locking member.

8. The jig as described in claim 5 further including a drill bit slidably positioned through the openings of the first leg and the second housing.

9. The jig as described in claim 1 further including means for releasably attaching the jig to the implant.

10. A method for inserting and attaching a perforated implant in an animal, comprising the steps of:
    placing the perforated implant over a first leg of a first member of a jig, the first leg having at least two holes extending therethrough;
    aligning at least one of the perforations with the holes in the first leg;
    inserting the jig and the implant into a predetermined position in the animal;
    inserting a drill bit through a housing of a second member of the jig, the housing having at least two holes extending therethrough;
    indexing the drill bit such that the drill bit is aligned with the perforations and holes in the first leg while in the inserted position;
    drilling a hole through a bone in the animal while the drill bit is in the indexed position;
    removing the drill bit from the jig;
    separating the first leg of the jig from the implant; and
    inserting a locking mechanism to secure the implant from migrating.

11. The method as described in claim 10 wherein the locking mechanism is a screw.

12. The method as described in claim 10 further including the step of placing bone marrow in the implant.

13. The method as described in claim 10 wherein the insertion is performed on the interphalangeal joint of an animal.

14. The method as described in claim 13 wherein the animal is a horse.

* * * * *